United States Patent
Enomoto et al.

(10) Patent No.: US 9,968,465 B2
(45) Date of Patent: May 15, 2018

(54) FEMORAL COMPONENT TRIAL FOR KNEE JOINT

(71) Applicant: KYOCERA Medical Corporation

(72) Inventors: Yuichi Enomoto, Kyoto (JP); Masahiko Hashida, Kyoto (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 315 days.

(21) Appl. No.: 14/775,080

(22) PCT Filed: Mar. 14, 2014

(86) PCT No.: PCT/JP2014/056943
§ 371 (c)(1),
(2) Date: Sep. 11, 2015

(87) PCT Pub. No.: WO2014/148393
PCT Pub. Date: Sep. 25, 2014

(65) Prior Publication Data
US 2016/0030198 A1 Feb. 4, 2016

(30) Foreign Application Priority Data
Mar. 19, 2013 (JP) .................................. 2013-056063

(51) Int. Cl.
*A61F 2/46* (2006.01)
*A61F 2/38* (2006.01)
*A61B 17/15* (2006.01)

(52) U.S. Cl.
CPC .......... *A61F 2/4684* (2013.01); *A61F 2/3859* (2013.01); *A61B 17/154* (2013.01); *A61B 17/155* (2013.01)

(58) Field of Classification Search
CPC .... A61F 2/4684; A61F 2/3859; A61B 17/155; A61B 17/154
See application file for complete search history.

(56) References Cited

U.S. PATENT DOCUMENTS 5,100,409 A    3/1992   Coates et al.
5,716,361 A *  2/1998   Masini ................. A61B 17/154
                                                              606/82
(Continued)

FOREIGN PATENT DOCUMENTS

EP    0502737 A1    9/1992
EP    2042111 A2    4/2009
(Continued)

OTHER PUBLICATIONS

Extended European Search Report, European Patent Application No. 14769963.1, dated Oct. 26, 2016, 7 pgs.
(Continued)

*Primary Examiner* — Christian Sevilla
(74) *Attorney, Agent, or Firm* — Volpe and Koenig, P.C.

(57) ABSTRACT

A femoral component trial for a knee joint of the present invention includes a trial body. The trial body includes a medial condyle and a lateral condyle that are located away from each other on an external surface, a through hole that is located between the medial condyle and the lateral condyle and has an approximately rectangular shape whose long side is an outer edge of an inner wall located along a back-and-forth direction and whose short side is an outer edge of an inner wall located along a right-and-left direction in an external surface view, a first guide slit that is located ahead of and above the through hole and extends in the right-and-left direction, and four second guide slits respectively extending from four corner parts of the through hole and along the long side.

6 Claims, 3 Drawing Sheets

(56) References Cited

U.S. PATENT DOCUMENTS

| | | |
|---|---|---|
| 2004/0153066 A1 | 8/2004 | Coon et al. |
| 2006/0173463 A1 | 8/2006 | Dees, Jr. |
| 2009/0088762 A1 | 4/2009 | Koenemann |
| 2011/0218541 A1 | 9/2011 | Bailey et al. |
| 2012/0123420 A1 | 5/2012 | Honiball |
| 2012/0323334 A1 | 12/2012 | Jones et al. |

FOREIGN PATENT DOCUMENTS

| | | | |
|---|---|---|---|
| GB | 2426200 A | * 11/2006 | ........... A61B 17/155 |
| GB | 2426200 A | 11/2006 | |
| JP | 06-133984 A | 5/1994 | |
| JP | 11-514906 A | 12/1999 | |
| JP | 2008-523962 A | 7/2008 | |
| JP | 3165932 U | 1/2011 | |
| JP | 2012-531242 A | 12/2012 | |
| WO | 97/016129 A1 | 5/1997 | |
| WO | 2006/069260 A1 | 6/2006 | |
| WO | 2010/150222 A1 | 12/2010 | |

OTHER PUBLICATIONS

International Search Report, PCT/JP2014/056943, dated Apr. 8, 2014, 2 pgs.

\* cited by examiner

FEMORAL COMPONENT TRIAL FOR KNEE JOINT

TECHNICAL FIELD

The present invention relates to a femoral component trial for a knee joint.

BACKGROUND ART

Conventionally, artificial knee joint placement technique has been carried out, with which a knee joint being functionally deteriorated is replaced with an artificial one. The artificial knee joint includes a femoral component to be placed on a femur and a tibial component to be placed on a tibia. Before these components are respectively placed on the bones, tools referred to as trials for fitting, whose shapes are respectively substantially the same as their corresponding components, are usually placed on the bones, and a trial reposition is carried out.

Here, in an artificial knee joint of the type having a post (projection) on a tibial component, such as PS (posterior stabilized) type one, it is necessary to cut an intercondylar area between a medial condyle and a lateral condyle on a distal end of the femur when a trial of the femoral component is placed on the femur. The cutting of the intercondylar area is usually carried out using a tool referred to as an intercondylar cutting guide in the following steps (i) to (iv) (see, for example, Patent document 1):

(i) attaching the intercondylar cutting guide to the distal end of the femur;
(ii) cutting the intercondylar area via the intercondylar cutting guide by using a bone cutting tool;
(iii) removing the intercondylar cutting guide from the distal end of the femur; and
(iv) placing the trial on the distal end of the femur after being subjected to the intercondylar cutting.

The conventional intercondylar cutting guide as described in Patent document 1 is made up of the trial and another tool. Therefore the above steps (i) to (iv) are necessary for the placement of the trial, thus leading to the problem that surgical time becomes longer. There is also the problem that the number of tools constituting a tool system is increased.

Patent document 2 describes a structure that secures an intercondylar cutting guide to a trial.

Even with the structure, it takes longer to secure the intercondylar cutting guide to the trial, thus leading to the problem that surgical time becomes longer. Similarly to Patent document 1 as described above, there is also the problem that the number of tools is increased.

PRIOR ART

Patent Documents

Patent Document 1: Japanese Utility Model Registration No. 3165932
Patent Document 2: Japanese Tokuhyo Publication No. 2008-523962

SUMMARY OF THE INVENTION

Problems to be Solved by the Invention

An object of the present invention is to provide a femoral component trial for a knee joint, which is capable of reducing surgical time and also decreasing the number of tools.

Means of Solving the Problems

A femoral component trial for a knee joint of the present invention includes a trial body. The trial body includes a medial condyle and a lateral condyle that are located away from each other on an external surface, a through hole that is located between the medial condyle and the lateral condyle and has an approximately rectangular shape whose long side is an outer edge of an inner wall located along a back-and-forth direction and whose short side is an outer edge of an inner wall located along a right-and-left direction in an external surface view, a first guide slit that is located ahead of and above the through hole and extends in the right-and-left direction, and four second guide slits respectively extending from four corner parts of the through hole and along the long side.

Effects of the Invention

The present invention includes the trial body having the first guide slit that is located ahead of and above the through hole and extends in the right-and-left direction, and the four second guide slits respectively extending from the four corner parts of the through hole and along the long side. Thus, the intercondylar cutting guide is configured integrally with the trial. Therefore, the intercondylar cutting of the femur and the placement of the trial are achievable at the same time, thus making it possible to decrease the number of surgical procedures so as to reduce surgical time. Additionally, it is possible to decrease the number of tools, thereby ensuring that cost reduction is attainable and misregistration due to tool replacement is suppressible.

EMBODIMENTS FOR CARRYING OUT THE INVENTION

A femoral component trial for a knee joint according to an embodiment of the present invention (hereinafter referred to generally as "trial") is described in detail below with reference to FIGS. 1 to 3. Arrows X, Y, and Z in FIGS. 1 to 3 indicate directions as viewed from a patient, namely, X1 indicates a forward direction, X2 indicates a backward direction, Y1 indicates a rightward (inward) direction, Y2 indicates a leftward (outward) direction, Z1 indicates an upward direction, and Z2 indicates a downward direction. Although the trial of the present embodiment is intended for a left knee joint, the present invention is not limited thereto. That is, it is easy to produce a trial for a right knee joint by a bilaterally mirror symmetric design. The following description illustrates the case of using the trial of the present embodiment that is intended for the left knee joint unless otherwise noted.

Figure 1:
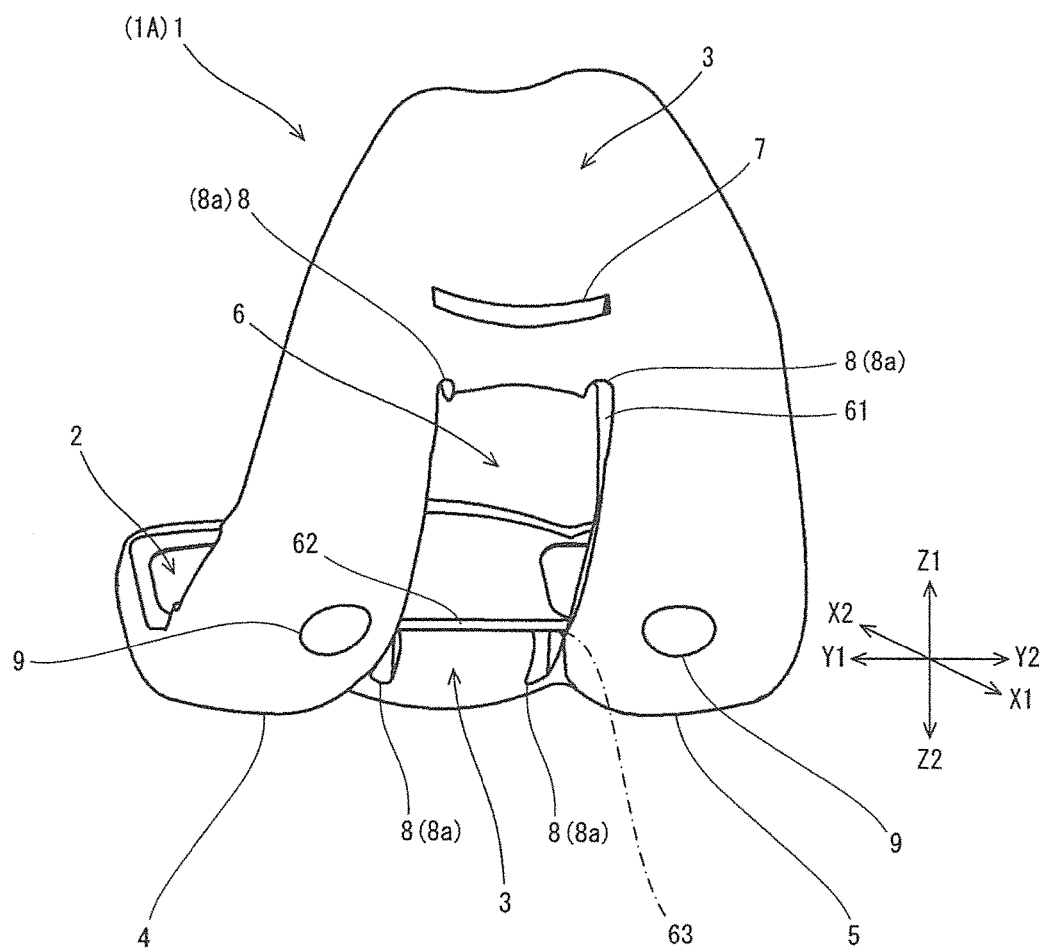
FIG. 1 is an enlarged perspective view showing a femoral component trial for a knee joint according to an embodiment of the present invention.
Figure 2A:
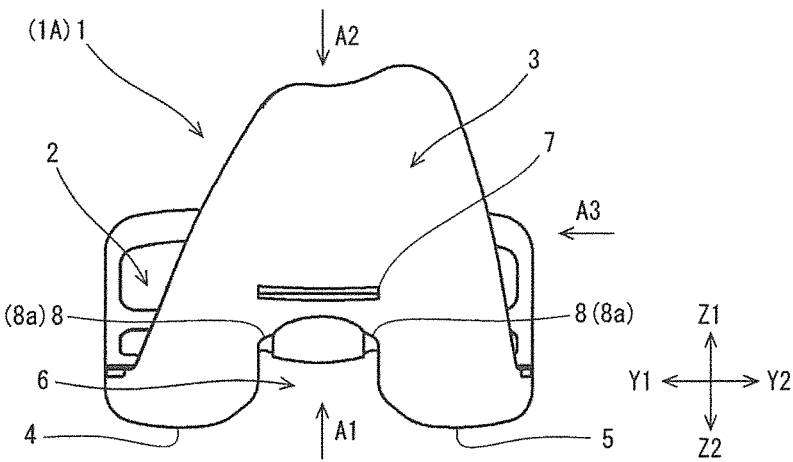
FIG. 2(a) is a front view of the femoral component trial for the knee joint shown in FIG. 1.
Figure 2B:
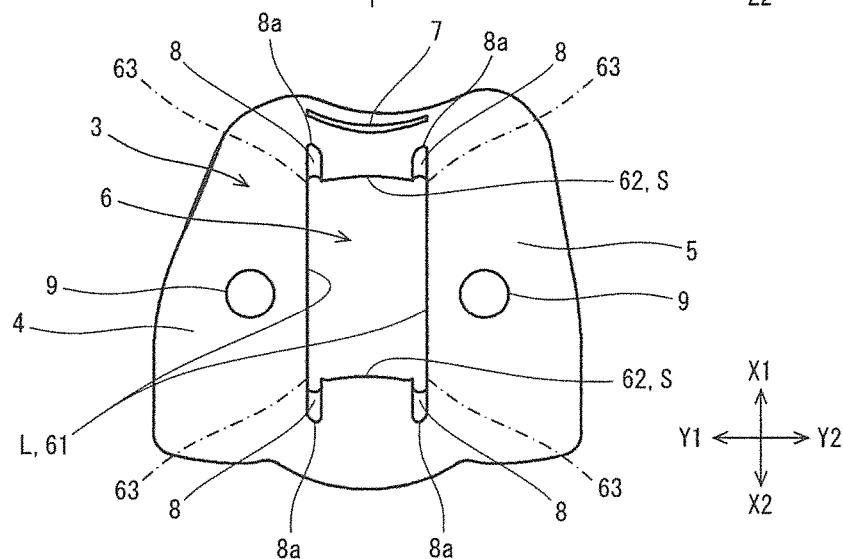
FIG. 2(b) is a bottom view thereof taken in the direction of arrow A1 in FIG. 2(a)
Figure 2C:
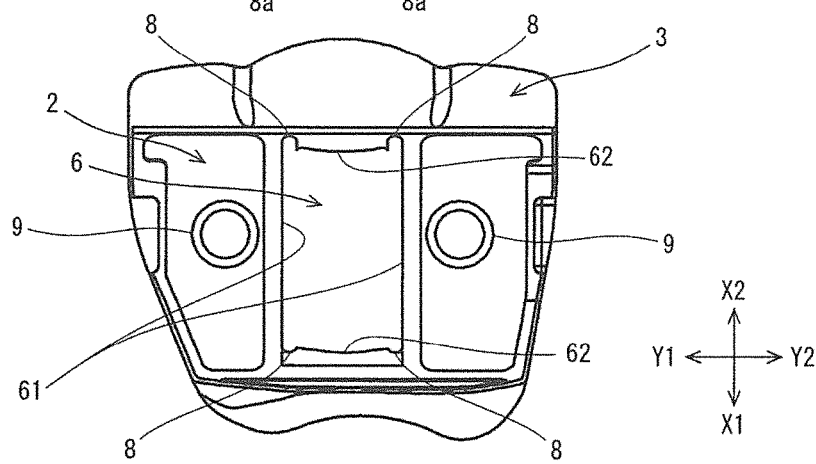
FIG. 2(c) is a plan view thereof taken in the direction of arrow A2 in FIG. 2(a)
Figure 3A:
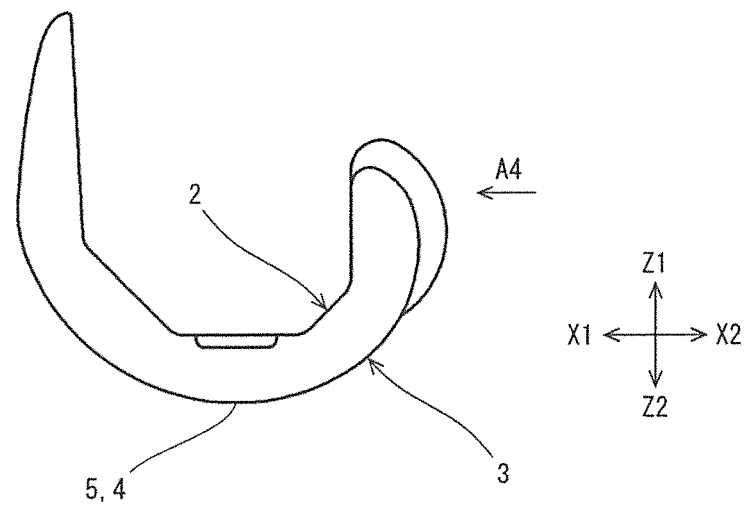
FIG. 3(a) is a side view of the femoral component trial for the knee joint shown in FIG. 1, taken in the direction of arrow A3 in FIG. 2(a)
Figure 3B:
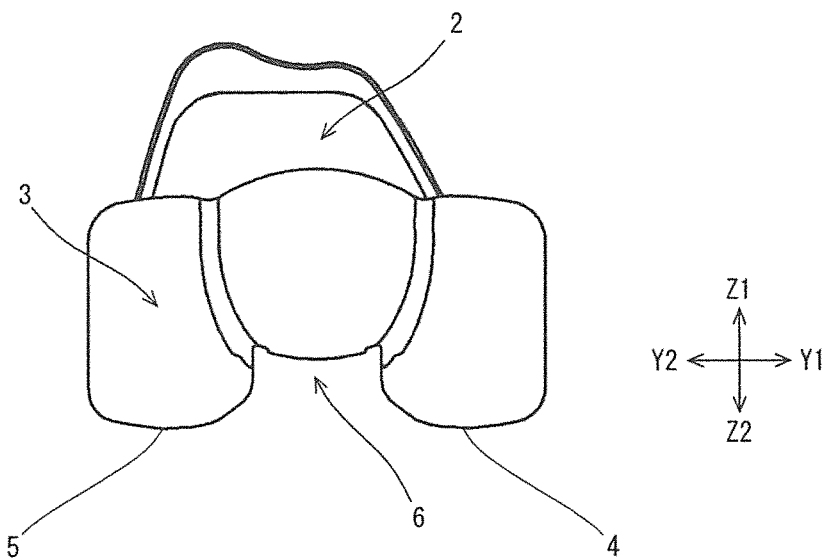
FIG. 3(b) is a rear view thereof taken in the direction of arrow A4 in FIG. 3(a).

As shown in FIGS. 1 to 3, the trial 1 of the present embodiment is a tool to be used for a trial reposition together with an unshown tibial component trial, and includes a trial body 1A. The trial body 1A of the present embodiment has an internal surface 2 and an external surface 3.

The internal surface 2 of the present embodiment is a surface of the trial 1 which is located close to a distal end of a femur when the trial 1 is placed on the distal end of the femur. The internal surface 2 of the present embodiment is made up of a plurality of flat surfaces.

A part of the external surface 3 of the present embodiment functions as a slide surface with respect to the tibial component trial. The trial body 1A of the present embodiment has a medial condyle 4 and a lateral condyle 5 that are located away from each other on the external surface 3. The trial body 1A of the present embodiment also has a through hole 6 located between the medial condyle 4 and the lateral condyle 5 in an external surface view. Here, the external surface view denotes a state in which the trial 1 is viewed from the external surface 3.

The through hole 6 of the present embodiment permits insertion of a post part of the tibial component trial and penetrates between the internal surface 2 and the external surface 3. The through hole 6 of the present embodiment has an approximately rectangular shape whose long side L is an outer edge of an inner wall 61 located along a back-and-forth direction and whose short side S is an outer edge of an inner wall 62 located along a right-and-left direction in the external surface view. This configuration ensures that an intercondylar area of the femur is exposed from the through hole 6 when the trail 1 is placed on the distal end of the femur.

The trial body 1A of the present embodiment includes a first guide slit 7 and second guide slits 8. The first guide slit 7 of the present embodiment is located ahead of and above the through hole 6 and extends along the right-and-left direction in the external surface view. The number of the second guide slits 8 of the present embodiment is four. The second guide slits 8 respectively extend along the long side L from four corner parts 63 of the through hole 6. These configurations produce the following effects.

That is, all of the first guide slit 7 and the second guide slits 8 function as the intercondylar cutting guide. Specifically, the first guide slit 7 is located ahead of and above the through hole 6. Hence, with the knee joint of the patient bent, a first bone cutting tool, such as a chisel, is insertable into the first guide slit 7 so as to be guided to the intercondylar area of the femur. The second guide slits 8 respectively extend from the corner parts 63 of the through hole 6 along the long side L and hence are connected to the inner wall 61. This allows a second bone cutting tool, such as a bone saw, to move along the inner wall 61 and the two second guide slits 8 connected to the inner wall 61. Consequently, the above configurations ensure that an intercondylar cutting in the femur is performable via the first guide slit 7 and the second guide slits 8 by using the first and second bone cutting tools.

Particularly, according to the present embodiment, the bone is cuttable along the second guide slits 8 with the first bone cutting tool, such as the chisel, inserted into the first guide slit 7 by using the second bone cutting tool, such as the bone saw. Consequently, the first bone cutting tool, such as the chisel, contributes to regulating a cutting depth of the bone by the second bone cutting tool, such as the bone saw, thereby achieving accurate bone cutting while avoiding unnecessary cutting of the bone.

With the above configuration, the intercondylar cutting guide is configured integrally with the trial 1. In other words, all of the first guide slit 7 and the second guide slits 8 are configured integrally with the trial body 1A. Therefore, the intercondylar cutting of the femur and the placement of the trial 1 are achievable at the same time. This makes it possible to decrease the number of surgical procedures so as to reduce surgical time. In the present embodiment, the first guide slit 7 and the second guide slits 8 are individually configured as inseparable from the trial body 1A.

The above configuration contributes to a decrease in the number of tools, thus making it possible to achieve cost reduction and suppress misregistration due to tool replacement.

A slit width of the first guide slit 7 of the present embodiment, which extends along a right-and-left direction thereof, is approximately identical with a length of the short side S. With this configuration, a width of the first bone cutting tool, such as the chisel, to be insertable into the first guide slit 7 coincides with a width of the intercondylar area of the femur to be exposed from the through hole 6, thus leading to improvement of intercondylar cutting accuracy.

In the present embodiment, as shown in FIG. 1, the four second guide slits 8 are respectively inclined so as to be closer to the external surface 3 as departing from the four corner parts 63. In other words, in the present embodiment, the four second guide slits 8 are respectively inclined so as to be closer to the external surface 3 as going from the four corner parts 63 to front end portions 8a of the second guide slits 8. This configuration ensures smooth movement of the second bone cutting tool, such as the bone saw, and also prevents an uncut portion of the bone in the vicinity of the front end portions 8a. An angle of inclination of the front end portions 8a is preferably 40 to 50°.

Alternatively, the four second guide slits 8 may have the same length or different lengths.

The trial 1 of the present embodiment further includes a pair of guide holes 9 and 9 that are respectively located on the medial condyle 4 and the lateral condyle 5. In the present embodiment, each of the pair of guide holes 9 and 9 penetrates between the internal surface 2 and the external surface 3 and has an approximately circular shape in the external surface view. With this configuration, a cutting tool, such as a drill, is insertable into each of the pair of guide holes 9 and 9 so as to be guided to the distal end of the femur, and peg holes that correspond to two pegs included in the femoral component are formable at the distal end of the femur.

The invention claimed is:

1. A femoral component trial for a knee joint, comprising:
a trial body comprising
   a medial condyle and a lateral condyle that are located away from each other on an external surface,
   a through hole that is located between the medial condyle and the lateral condyle and has an approximately rectangular shape whose long side is an outer edge of an inner wall located along a back-and-forth direction and whose short side is an outer edge of an inner wall located along a right-and-left direction in an external surface view,
   a first guide slit that is located ahead of and above the through hole and extends in the right-and-left direction, and
   four second guide slits respectively extending from four corner parts of the through hole and along the long side.

2. The femoral component trial for a knee joint according to claim 1, wherein each of the first guide slit and the second guide slits is configured as inseparable from the trial body.

3. The femoral component trial for a knee joint according to claim 1, wherein a slit width of the first guide slit, which extends along a right-and-left direction thereof, is identical with a length of the short side.

4. The femoral component trial for a knee joint according to claim 1, wherein the four second guide slits are respectively inclined so as to be closer to the external surface as departing from the four corner parts.

5. The femoral component trial for a knee joint according to claim 1, wherein a first bone cutting tool to be guided via the first guide slit is a chisel, and a second cutting tool to be guided via the four second guide slits is a bone saw.

6. The femoral component trial for a knee joint according to claim 1, further comprising:
   a pair of guide holes that are respectively located on the medial condyle and the lateral condyle.

* * * * *